(12) United States Patent
White

(10) Patent No.: US 11,432,741 B2
(45) Date of Patent: Sep. 6, 2022

(54) OXYGEN MASK RESPIROMETER

(71) Applicant: Child Mind Institute, Inc., New York, NY (US)

(72) Inventor: Curtis P. White, Queens, NY (US)

(73) Assignee: Child Mind Institute, Inc., New York, NY (US)

(*) Notice: Subject to any disclaimer, the term of this patent is extended or adjusted under 35 U.S.C. 154(b) by 0 days.

(21) Appl. No.: 16/816,220

(22) Filed: Mar. 11, 2020

(65) Prior Publication Data
US 2021/0282665 A1 Sep. 16, 2021

(51) Int. Cl.
*A61B 5/08* (2006.01)
*A61B 5/00* (2006.01)
*A61B 5/083* (2006.01)

(52) U.S. Cl.
CPC .......... *A61B 5/0816* (2013.01); *A61B 5/0833* (2013.01); *A61B 5/6803* (2013.01); *A61B 5/742* (2013.01); *A61B 2562/029* (2013.01); *A61B 2562/0219* (2013.01); *A61B 2562/0247* (2013.01); *A61B 2562/0271* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,063,938 A | * | 11/1991 | Beck | A61B 5/0816 128/200.26 |
| 2004/0163648 A1 | * | 8/2004 | Burton | A61M 16/0633 128/204.21 |
| 2007/0129643 A1 | * | 6/2007 | Kwok | A61B 5/0816 600/529 |
| 2014/0142403 A1 | * | 5/2014 | Brumback | A61B 5/681 600/324 |
| 2016/0029973 A1 | * | 2/2016 | Kahlman | A61B 5/015 600/301 |
| 2016/0150981 A1 | * | 6/2016 | Baker | G06F 19/00 600/479 |
| 2017/0251933 A1 | * | 9/2017 | Braun | A61B 5/02055 |
| 2018/0078798 A1 | * | 3/2018 | Fabian | A61B 5/6803 |
| 2019/0175064 A1 | * | 6/2019 | Haveri | A61B 5/0878 |
| 2019/0362822 A1 | * | 11/2019 | Haveri | G08B 5/36 |
| 2020/0085370 A1 | * | 3/2020 | Hill | A61B 5/4818 |

OTHER PUBLICATIONS

Jeong et al. Measurement of Respiration Rate and Depth Through Difference in Temperature Between Skin Surface and Nostril by Using Thermal Image. (Year: 2018).*

* cited by examiner

Primary Examiner — Etsub D Berhanu
(74) Attorney, Agent, or Firm — Kelley Drye & Warren LLP

(57) ABSTRACT

Devices, systems, and methods for monitoring respiration using surface temperature, humidity, air pressure, carbon dioxide gas sensors, pulse oximetry sensors and electromyography sensors, and/or acceleration sensors to obtain information related to respiration rate (RR), exhalation/inhalation strength, exhalation/inhalation volume, exhalation/inhalation acceleration, and/or exhalation/inhalation regularity.

20 Claims, 5 Drawing Sheets

OXYGEN MASK RESPIROMETER

BACKGROUND OF THE INVENTION

Vital sign monitoring is a crucial and universal component of monitoring patient health and diagnosing pathologies. Four vital signs broadly accepted by the medical community for monitoring patients are pulse rate, blood pressure, respiratory rate and body temperature. An abnormal respiratory rate has been shown to be an important predictor of serious events such as cardiac arrest and admission to an intensive care unit. In 1993, Fieselmann and colleagues reported that a respiratory rate higher that 27 breaths per minute was the most important predictor of cardiac arrest in hospital wards. They further found that in unstable patients, relative changes in respiratory rate were much greater than changes in heart rate or systolic blood pressure, and thus that the respiratory rate was likely to be a better means of discrimination between stable patients and patients at risk. Respiratory rate is an important indicator of a severe problem in many body systems, not just the respiratory system, and is therefore a key predictor of adverse events. Yet, recent studies have shown that accurate and consistent monitoring and recordation of vital signs in hospital settings is poor. Respiratory rate is often not regularly recorded, even when the patient's primary health issue is a respiratory condition.

Two common methods used to monitor respiration in a vital sign context are pulse oximetry and breath counting/timing. Pulse oximetry, however, does not provide an accurate measure of respiration rate. Any respiration rate measurements displayed by a pulse oximeter are approximations based on cross population correlation between respiration rate and SpO2. Pulse oximeters do not provide information necessary to determine accurate respiration rate measurements. Pulse oximeters are also relatively inaccurate. A patient's skin color, body fat, body movement, and preexisting vascular condition can interfere with the ability of a pulse oximeter to monitor respiration.

The method of counting and timing patient breaths can accurately measure respiration rate under ideal conditions, but in practice it is often woefully inadequate. It is time consuming, requires mental calculations or use of a calculator, and when compared to computerized heart rate monitors or a thermometer, is extremely tedious. It is also labor intensive and prone to error, both of which can raise expenses for medical care providers. Compliance of hospital staff with breath counting respiration rate monitoring is very low.

Respiration monitoring is often used in sleep studies for the purpose of diagnosing and/or monitoring sleep disorders and breathing disorders like sleep apnea. However, sleep studies are expensive and time consuming. There are few sleep study centers in the United States. People with time-intensive family obligations such as single mothers or individuals who do not have access to transportation may be unable to participate in a full sleep study. Although the present invention cannot entirely replace a sleep study, it can provide much of the information used in a sleep study—more than any other consumer product currently available. The present invention therefore can be used to diagnose and monitor disorders such as sleep apnea. A low-cost wearable device such as the present invention can at the very least act as a screening tool to determine who is in most need of a sleep study.

SUMMARY OF THE INVENTION

The present invention is a novel respiration monitor that makes use of surface temperature, humidity, air pressure and acceleration sensors to obtain information related to respiration rate (RR), exhalation/inhalation strength, exhalation/inhalation volume, exhalation/inhalation acceleration, exhalation/inhalation regularity and respiration related symptoms pertaining to sleep apnea and other diseases. It may also make use of carbon dioxide gas sensors, pulse oximetry sensors and electromyography sensors. This respiration monitor is worn proximate to the face in a fashion which allows access to exhaled gas in isolation from surrounding air. In one embodiment, the device may be built into or mounted onto an assistive oxygen mask. The device might also be used in conjunction with a dust mask or surgical mask. The device might also be used in conjunction with life-supporting ventilation masks or masks used to administer general anesthesia. The device might also be used in conjunction with assistive oxygen nasal cannula by using a funnel or channel to direct exhaled gas from the mouth and nose towards the device sensors.

Numerous variations may be practiced in the preferred embodiment.

BRIEF DESCRIPTION OF THE DRAWINGS

A further understanding of the invention can be obtained by reference to exemplary embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

DETAILED DESCRIPTION OF THE INVENTION

Figure 1:
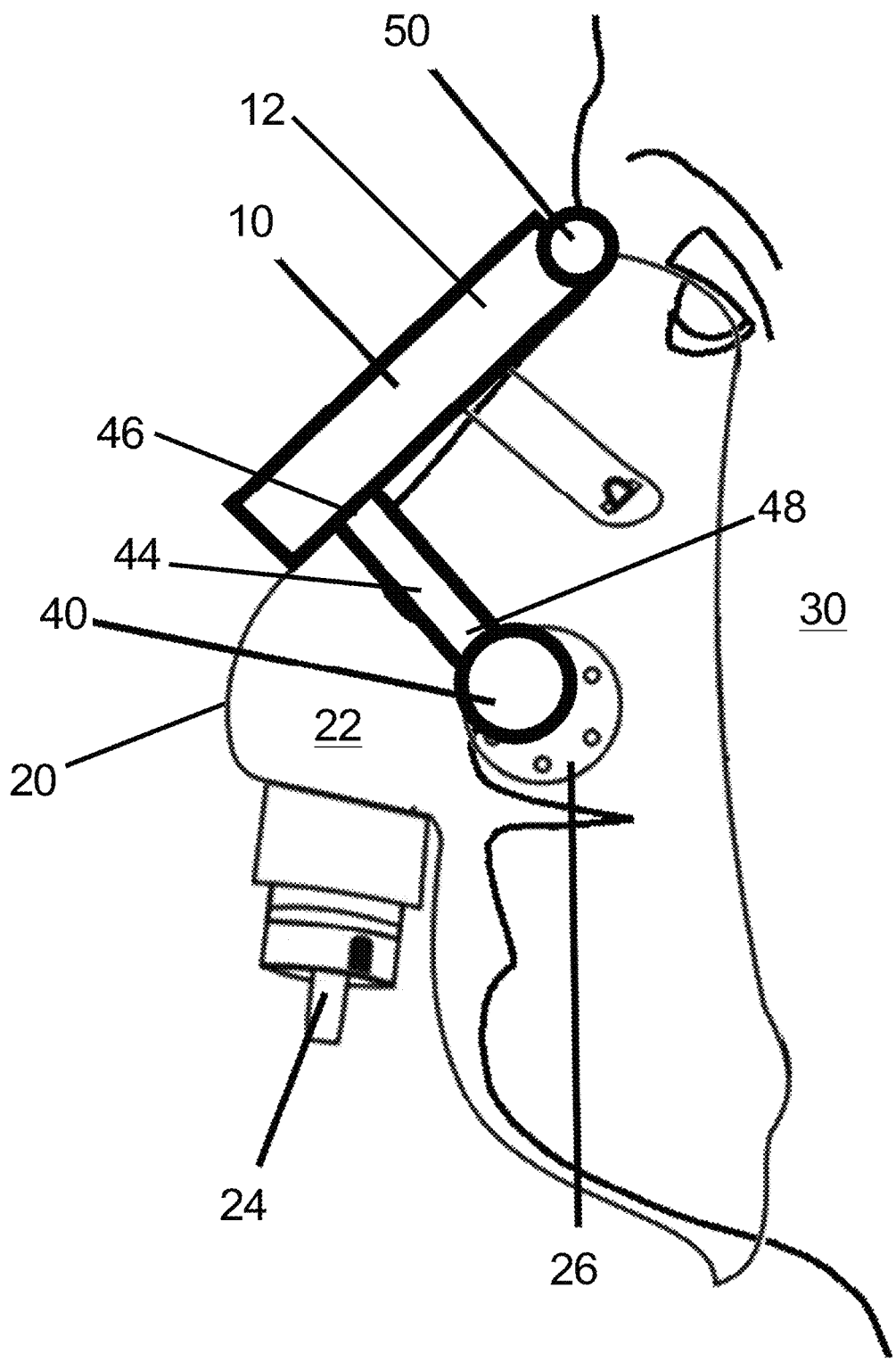
FIG. 1 depicts an embodiment of the present invention.

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Use of the term "exemplary" means illustrative or by way of example, and any reference herein to "the invention" is not intended to restrict or limit the invention to the exact features or steps of any one or more of the exemplary embodiments disclosed in the present specification. Also, repeated use of the phrase "in one embodiment," "in an exemplary embodiment," or similar phrases do not necessarily refer to the same embodiment, although they may. It is also noted that terms like "preferably," "commonly," and "typically" are not used herein to limit the scope of the claimed invention or to imply that certain features are critical, essential, or even important to the structure or function of the claimed invention. Rather, those terms are merely intended to highlight alternative or additional features that may or may not be used in a particular embodiment of the present invention.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

Analysis of gas exhaled by a person, including the temperature of the exhaled gas, has often been used to monitor respiration. However, directly measuring the temperature of exhaled gas presents several hurdles. First, gas temperature sensors only measure the temperature of gas that is immediately adjacent to the sensor. Because a gas temperature sensor takes a point measurement, the temperature reported by a temperature sensor often is not representative of overall exhalation temperature. This problem is further exacerbated by the fact that the ideal placement of a gas temperature sensor to monitor exhalation temperature would be directly in the path of exhalation, i.e. directly over the mouth or nose where the sensor may impede or block breathing.

Second, exhaled gases are not thermally conductive, which makes change in temperature corresponding to respiration over time difficult to use for the purposes of respiration monitoring. The path of dissemination for exhaled gas is also unpredictable due to movement of a patient, air eddying produced by face geometry or proximate objects such as a mask, and/or surrounding air movement such as wind. Dissemination of exhaled gas has a larger impact on measured exhalation temperature than decrease in temperature over time caused by contact of the surrounding environment which is usually cooler than body temperature.

The present invention may use a thermopile surface temperature sensor to indirectly monitor temperature of exhaled gas. The inside of an assistive oxygen mask constitutes a contained area in which exhaled gas is isolated from the surrounding air. Because exhaled gas is typically warmer than ambient air, the exhaled gas may warm the surface of the subject's skin where it is covered by the mask, as well as the surface of the mask itself and areas of the mask directly exposed to exhaled gas exiting the mask. The thermal energy conducted from exhaled gas is typically only sufficient to warm the surface of these objects. Once exhalation is complete, the surface of these objects will quickly cool at a predictable rate over time.

The present invention may use a thermopile sensor, such as a Melexis MLX90615 thermopile sensor, to measure the temperature of surfaces inside an oxygen mask or surfaces proximate to the path of exhalation leaving the oxygen mask through mask vents. This sensor has a 120 degree view angle. The surface area of the base of a cone can be found as follows: AREA=π(DISTANCE tan(ANGLE))^2. So if a sensor with a 120 degree view angle is placed 3 centimeters from a surface, the resulting surface temperature would be the average surface temperature of an area 84.82 cm^2 in size. This is a significant improvement over point measurements provided by gas temperature sensors.

In one embodiment, the thermopile sensor may be attached to an assistive oxygen mask, for example mounted on the inside of an assistive oxygen mask. The thermopile sensor may be pointed towards the subject's skin immediately proximate to the mouth. Because a thermopile sensor can measure surface temperature from a certain distance, unlike a gas temperature sensor, a thermopile sensor can be placed in a position where it does not risk impeding breathing. Because the thermopile sensor measures the average temperature over a large area exposed to exhalation, measured temperature is representative, unlike the temperature measured from a gas sensor point reading. Also, because the surface temperature inside the oxygen mask cools in a measurable fashion after exhalation, change in temperature over time is easier to measure. Although surface temperature only provides a relative measure of exhalation temperature—determined by the change in surface temperature of a patient's skin around the patient's mouth when the patient's breath passes over the skin as the patient exhales while wearing a oxygen mask—absolute temperature of exhaled gas is not particularly important to respiration monitoring. Note that the term "patient" is used herein to connote any person who uses or for whom is used a device, system, or method in accordance with the present invention; the term "patient" is not intended to limit the context or scope of the invention to monitoring of medical patients.

A device, system, or method in accordance with the present invention may include and record data concerning, for example, exhalation from a patient, from one or more sensors.

Referring to FIG. 1, device (10) according to the present invention may be attached to the outside of assistive oxygen mask (20). Device (10) may include housing (12) and sensor head (40). Sensor head (40) may be attached to housing (12) by, for example, an adjustable arm (44). Adjustable arm (44) may extend from a first end (46) to a second end (48). Adjustable arm (44) may be capable of retaining sensor head (40) in one or more positions relative to housing (12). For example, a first hinge at first end (46) may allow adjustable arm (44) to pivot relative to housing (12) and retain adjustable arm (44) in a position relative to housing (12). A second hinge at second end (48) may allow sensor head (40) to pivot relative to adjustable arm (44) and retain sensor head (40) in a position relative to adjustable arm (44).

Device (10) may be permanently affixed to mask (20) with, for example, a fastener on the outer surface of housing (12) such as an adhesive or an interference fit between mating elements on device (10) and mask (20) (not shown). Alternatively, device (10) may be temporarily affixed to mask (20) with, for example, a fastener on outer the surface of housing (12) such as Velcro (hook-and-loop material), snaps, or the like. A rubber clip (50) may be used to help secure device (10) to mask (20).

When mask (20) is worn by patient (30), cavity (22) is formed between mask (20) and the face of patient (30). Oxygen may be pumped into cavity (22) at entrance (24), and exhaled gas (along with excess oxygen) may exit mask (20) through vent (26). Device (10) may be affixed to the center, front of mask (20). A display (270) and/or touch screen (250) may be on the top, side, or bottom of device (10). Display (270) may be, for example, an OLED display, an LCD display, or any other type of display. Display (270) and/or touch screen (250) may be visible and accessible while device (10) is attached to mask (20).

Figure 2:
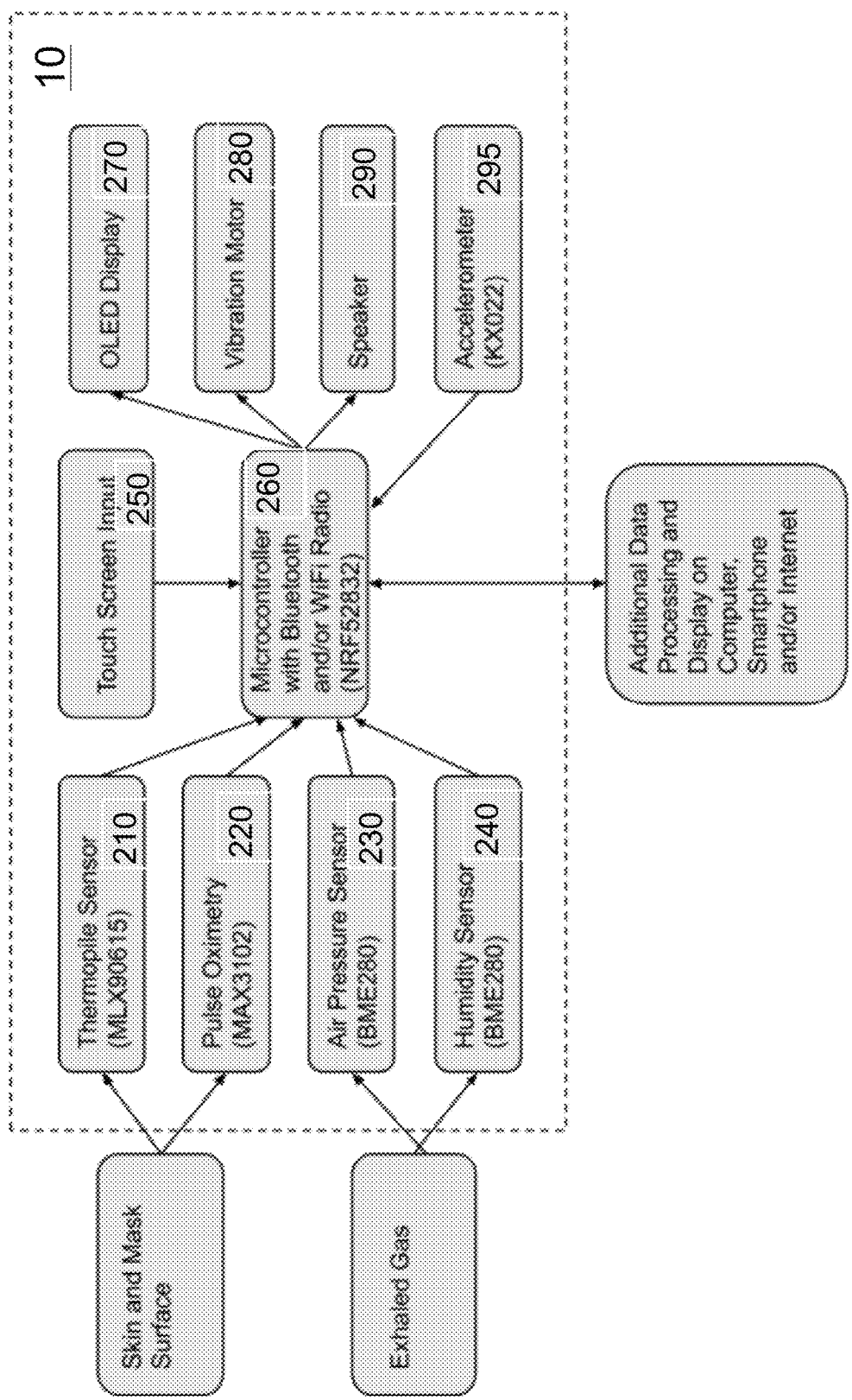
FIG. 2 depicts an exemplary block diagram of components of an embodiment of the present invention.

Referring to FIG. 2, device (10) may include one or more sensors including one or more temperatures sensors (210) (e.g. thermopile sensors) that may be used to measure, for example, surface temperature or changes in surface temperature, one or more pulse oximeters (220), one or more pressure sensors (230) that may be used to measure, for example, air pressure or changes in air pressure, one or more hygrometers (240) that may be used to measure, for example, humidity or changes in humidity, one or more accelerometer sensors (295) that may be used to measure, for example, body movement or changes in body movement, and/or one or more carbon dioxide monitors (not shown) that may be used to measure, for example, carbon dioxide content or changes in carbon dioxide content. RR and other respiration related information can be derived from data recorded from one or more of those sensors.

Housing (12) may contain a microcontroller, a memory (e.g. FLASH memory), power management circuitry, a radio, an accelerometer, an OLED display, a touch screen, a vibration motor, a speaker and/or a rechargeable battery. Housing (12) may be formed from any suitable material, such as plastic or metal. Housing (12) may have any suitable shape capable of enclosing the components situated therein, such as a cylinder or a rectangular box.

Sensor head (40) may be placed over mask vent (26). Sensor head (40) may contain a thermopile surface temperature sensor, an air pressure sensor and/or a humidity sensor. These sensors may be connected to circuitry, a microcontroller and/or a memory within housing (12) by wires which pass through adjustable arm (44). The thermopile sensor may be pointed toward the face of patient (30) and receive thermal radiation of the patient's skin surface through the mask vent (26). Exhaled gas may be driven through the vent, into the air pressure and humidity sensors mounted within sensor head (40).

Because a patient's forehead is an ideal area to obtain pulse oximetry readings, a pulse oximeter (220) may be mounted in a rubber clip (50) which may slide onto the top edge of oxygen mask (20). The pulse oximeter may be connected to a processor, circuitry, and/or memory within housing (12) with wires embedded in elastic rubber.

Certain situations, conditions, or circumstances in which device (10) may be used could limit the usefulness of data provided by one or more of the sensors within device (10). For example, ambient humidity may vary greatly depending on geographic location, time of year and local weather conditions. Exhaled gas typically has a relative humidity of 100%. In certain areas, the surrounding air can reach 100% relative humidity. If surrounding air and exhaled gas both have 100% relative humidity, a humidity sensor could not be used to measure RR or other respiration related information based on a change in humidity caused by exhaled gas—there would be no change in humidity for the sensor to detect each time the patient exhales because the exhaled gas would not cause any change in humidity. Similarly, wind, a fan, or sudden movement can interfere with a pressure sensor's ability to accurately measure change in air pressure at or around a patient's mouth caused when a patient exhales. Further, if ambient temperature approaches 37° C., the temperature of exhaled gas cannot be differentiated from the temperature of the surrounding air, interfering with a temperature sensor's ability to measure change in temperature when a patient exhales.

In one embodiment of the present invention, the potential individual weaknesses of each sensor may be overcome by combining and comparing data received by two or more different types of sensors. RR may be used as a baseline for determining which sensors are performing the best. An autocorrelation algorithm targeting the RR range may be applied to data from all the device's sensors. If a sensor's data correlates strongly to a potential RR pattern, the data would be prioritized for further analysis. If a sensor's data does not correlate strongly to a sine wave (or other regular pattern representing respiration) in the RR range, the data would not be prioritized for further analysis.

Once sensor prioritization has been determined using, for example, RR autocorrelation, sensor data from one or more sensors may be analyzed to extract and identify additional, potentially non-periodic, information about the user's respiration. The value of the combined sensors' data may be greater than the sum of its components. Each sensor may capture a particular aspect or characteristic of a target signal. In addition, machine learning techniques such as neural networks can be used to process the increased volume and diversity of data in training and activating models.

During respiration, the movement of a patient's diaphragm produces secondary movement throughout the body, especially in the upper torso, neck and head. Under ideal conditions, an accelerometer sensor (295) contained in the device can measure this movement, allowing for the determination of RR based on body movement alone. Although movement of the patient's body caused by the patient or environmental conditions (movement in a car, for example) can overwhelm the relatively minor movement produced by respiration, even fractional or degraded respiration movement data can be used as part of a larger data set, including data from other sensors, to determine RR. An accelerometer (295) can also add additional functionality providing data indicating step count (pedometer) which may be recorded and displayed by the device.

The relationship between device components can be observed in their relationship with the microcontroller. As shown in FIG. 2, a System on a Chip (SoC) (260), such as a Nordic NRF52832 microcontroller (MCU), may be included in device (10). The SoC may contain, for example, a Bluetooth radio and processor such as an ARM Cortex M4 MCU which runs at 64 MHz. The microcontroller preferably has sufficient computational power to perform autocorrelation, peak detection, Fourier transforms, simple digital filtering and simple neural network activation functions. With that computational power, the microcontroller may be used to may determine RR, RR regularity, shortness of breath, breath depth and other common respiration features. Data from device sensors can be transmitted wirelessly or by wire to, for example, a computer, a server, or the internet (data centers and cloud software) where additional computational power may allow for more sophisticated analysis.

Display (270) may communicate RR and other information to clinicians and caretakers. Touch screen (250) or other inputs on device (10), such as buttons, may allow for navigation of a user interface displayed on display (270). A vibration motor (280) and/or speaker (290) may provide a notification to the patient and/or nearby caretakers, such as an emergency notification, a notification that device (10) is not able to determine RR based on the data, or lack thereof, received from the sensors.

Figure 3A:
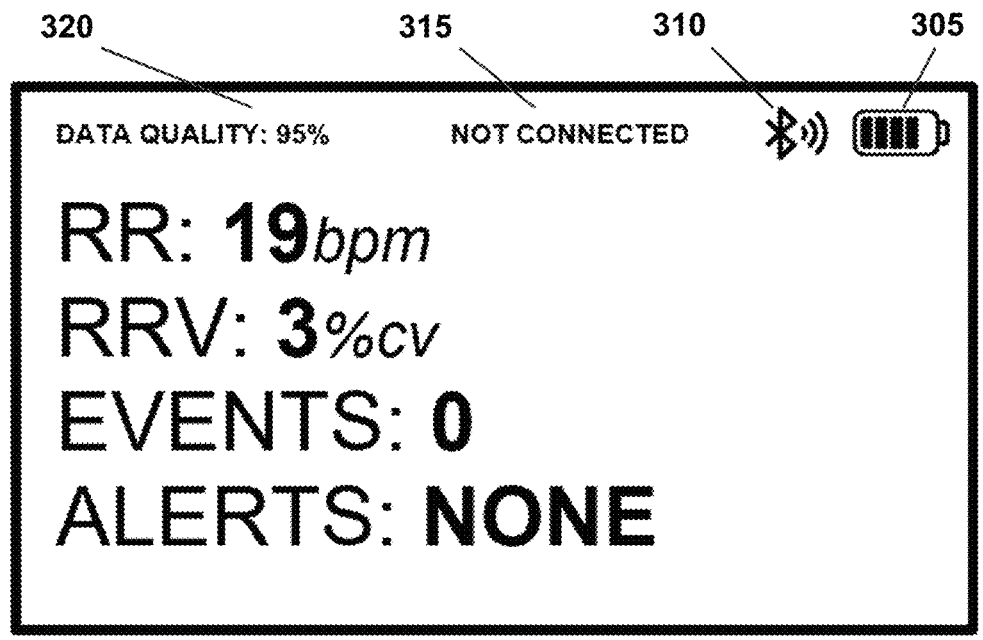
FIGS. 3A-3C depict exemplary device consoles.
Figure 3B:
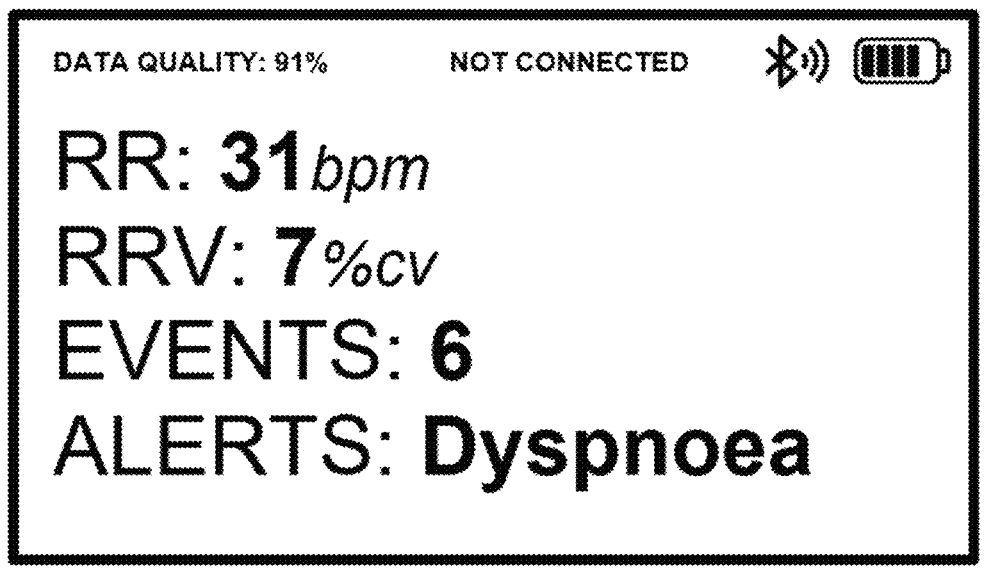
Figure 3C:
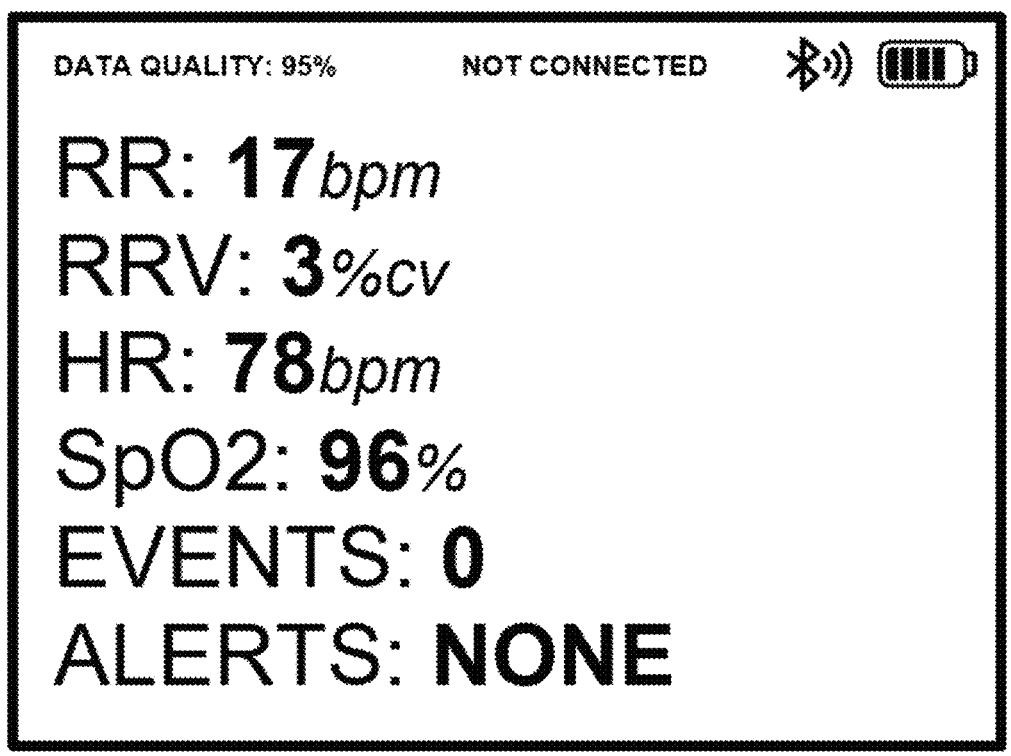

FIGS. 3A-3C depict exemplary consoles that may be provided on display (270) of the device (10). FIG. 3A depicts a console displaying battery charge (305), wireless connectivity availability (310), wireless connectivity status (315), and data quality (320). "Data quality" may indicate to a user that the position and/or location device (10) may need to be adjusted to receive a data transmission. Also displayed may be respiration rate (RR), and/or respiration rate variability (RRV) measured as the coefficient of variation percentage (CV). RR and RRV may be based on a 30 second sampling period. Device (10) may be programmed to detect a number of abnormal breathing patterns or notable respiratory events, such as Tachypnoea, Bradypnoea, Apnea, Dyspnoea, Cheyne-Stokes, Ataxic Breathing, and/or Hyperventilation. The console may display "ALERTS" indicating, for example, a detected abnormal breathing pattern or notable respiratory event.

Device (10) may be configured to receive an input from a user (e.g., the user tapping a finger) on display (270). Tapping on the display (270) may page through a list of detected respiratory events if any have been logged in memory of device (10). The respiratory events may be time-stamped. An "EVENTS" counter on display (270) may indicate the number of logged events available for review. Important events or phenomena that might require immediate attention may be directly noted in the "ALERTS" section. Display of an "ALERT" may coincide with a further buzzer notification or signal to the user, such as vibration from a vibration motor or an alert transmitted to another device via a wired or wireless computer connection.

FIG. 3B depicts a console display (270) indicating a distressed patient. RR and RRV are shown as elevated, corresponding to respiratory distress. The console indicates that six respiratory events have been logged and may be available for viewing. The "ALERTS" section indicates that the user may be experiencing Dyspnoea (i.e., difficulty breathing, gasping for air).

FIG. 3C depicts a console display (270) indicating that data (e.g., SpO2) has been received from a pulse oximeter included in device (10).

Discussed below are three exemplary algorithms that may be used to calculated RR according to the present invention: (1) peak detection; (2) autocorrelation; and (3) Fast Fourier Transform (FFT).

When a patient wears an oxygen mask, as the patient breathes out, the exhaled air may heat the surface of the skin around the patient's mouth to, for example, 93° F. As the patient breathes in, drawing air into the oxygen mask, the air drawn into the mask may reduce the temperature of the surface of the skin around the patient's mouth to, for example, 86° F. As described above, thermopile surface temperature sensor (210) in device (10) may be used to detect the temperature of the surface of the skin around the patient's mouth without obstructing the patient's breathing. Peak detection may be used to calculate the patient's RR by first selecting a pre-set threshold temperature, such as 90° F. RR may then be determined by recording the amount of time elapsed between the times at which the temperature reading exceeds the threshold temperature, and the times at which the temperature reading falls below the threshold temperature.

Additionally or alternatively, using autocorrelation, the correlation of sensor data to an array of sin waves (0.1 Hz, 0.125 Hz . . . 0.3 Hz) may be calculated. Whichever sin wave (if any) has the greatest correlation corresponds to the RR. If, for example, a patient's RR is 18 bpm (0.3 Hz), then the 0.3 Hz sin wave will be most closely correlated to the data. The same algorithm can be used to detect abnormal breathing patterns in addition to RR.

FFT transforms temporal data into frequency domain data. FFT may be used to determine at what frequency the data has the highest amplitude. For example, if a patient's RR is 18 bpm, a FFT spectrogram of the device sensor data should indicate a spike at 0.3 Hz.

Data analysis may be executed in real-time by the device on two types of signals. First are periodic signals, pseudo-periodic signals, and characteristics of periodic signals that are inherent to respiration, such as RR (Respiration Rate) and RRV (Respiration Rate Variability). These signals are expected to be present at all times, and the device may continuously detect, display, log and/or transmit the determined values. Second are respiration features or events that may be intermittent and complex in nature. These may be predefined by the user and/or when the device is manufactured, and may include diagnostic indicators of respiratory disorders, or events. One example of a respiratory disorder is sleep apnea, which may be detected by the device by, for example, sensing cessation of breathing for 10 seconds or longer from 5 to 100 times an hour. Each incidence of breathing cessation over 10 seconds could be detected by the device and logged as a sleep apnea event.

Figure 4:
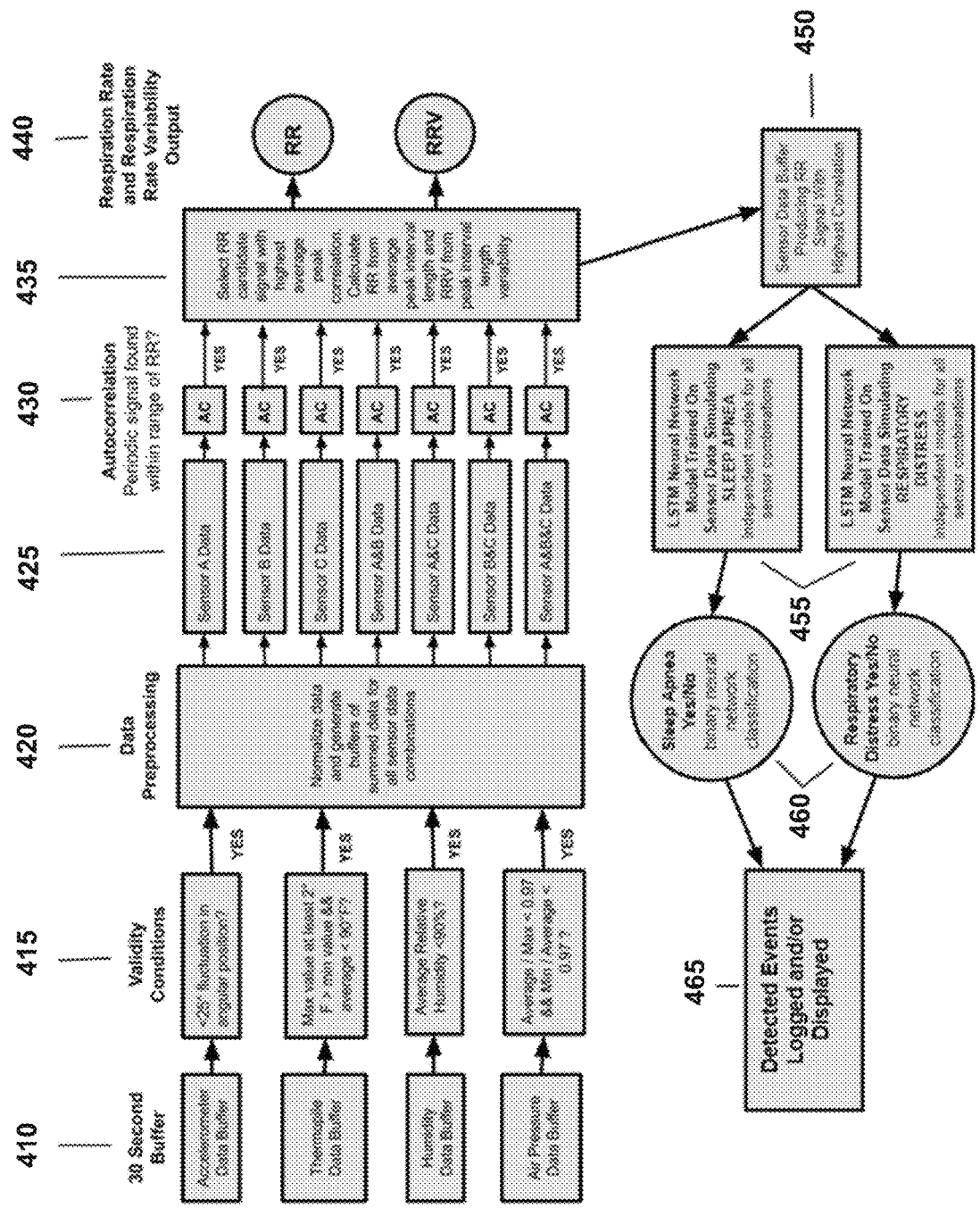
FIG. 4 depicts a flowchart in accordance with the present invention.

FIG. 4 is a flowchart showing an example of on-device data analysis according to the present invention. Sensor data from one or more sensors may be stored in a buffer (410). The buffer may have a duration of, for example, 30 seconds as shown in FIG. 4. Thirty seconds is a common observation duration for determining RR and RRV. Alternatively, the buffer may have a duration that is longer or shorter than 30 seconds. The buffer may have a sample rate of, for example, 10 Hz. Alternatively, the sample rate may be lower or higher than 10 Hz.

As discussed above, performance of the one or more sensors used in the device (e.g., thermopile surface temperature sensor, air pressure sensor, humidity sensor, accelerometer) can be degraded by environmental conditions. Under ideal circumstances, any one of the one or more sensors can provide data adequate for determining RR and/or RRV. However, circumstances are rarely ideal and a device used for monitoring vital signs preferably works in any condition.

Determining which of the one or more sensors are providing the most useful information may be crucial to device function. A validity condition (415) may be established for each of the one or more sensors. For example, a condition may consist of a cutoff that must be met. The cutoff may be, for example, a predetermined threshold sensor data value, a predetermined range of sensor data values, or a percentage change in sensor data values.

For example, when air is inhaled it typically becomes saturated with water. Under normal climate-controlled conditions like those commonly found in a hospital, a patient's exhalation typically has a markedly higher relative humidity than surrounding air. Each time the user patient exhales, water-saturated air comes into contact with the humidity sensor inside the device, increasing the humidity sensor values. As the exhalation dissipates between breaths and surrounding air enters the device, the humidity sensor values decrease. This cyclical fluctuation in humidity constitutes a periodic signal which is equivalent to RR. However, air can only hold so much water. Exhalations are often very close to the maximum saturation point of air: 100% relative humidity. In many climates, the water content of the air in the environment can approach 100% relative humidity. When ambient relative humidity and exhalation relative humidity approach each other, there is no longer a cyclical fluctuation in humidity sensor values and RR cannot be calculated from this signal. For this reason, when the average humidity detected by the device approaches 100% relative humidity, data from the humidity sensor may be considered invalid (415). Similarly, when the ambient temperature approaches human skin temperature, data from the thermopile sensor becomes less valid for determining RR.

Determining RR, much less RRV, from a change in body position is difficult because there are so many ways and so many reasons the user's body or parts of the user's body might move other than diaphragm expansion and compression during respiration. Because of this, if the angular position of the body shifts a large amount within the sample period, accelerometer data is considered less valid for determining RR.

There are many situations in which air pressure might fluctuate in a fashion that might degrade the device's ability to determine RR. For example, the user might alternate between breathing through the mouth and breathing through the nose, or a gust of wind or air from a fan might mask pressure fluctuation generated by respiration. Air pressure sensor data validity conditions meant to filter out outlier data can be used to ensure that air pressure sensor data is useful for determining RR and RRV. In these examples, simple cutoff values may be used to validate or invalidate data from individual sensors. Alternatively, more complex techniques can be used to refine this process. Instead of simple cutoff values, a function or model that takes into account complex conditions could dynamically determine sensor data validity. Instead of sensor data being either valid or invalid, a weighting system can be used to emphasize or deemphasize the significance of a particular sensor at any given time for accurately determining RR and RRV.

Once sensor data validity has been determined, sensor data in each 30 second buffer may be normalized and, if data from more than one sensor is determined to be valid, additional combined data buffers (e.g., arrays) may be generated for every combination of sensors with valid data. The combination of data buffers from individual sensors into a merged buffer may be executed in a fashion that maximizes acquisition of RR, for example, summation modified to emphasize a particular sensor based on initial sensor data validity determination. The intelligent combination of sensor data prior to the analysis of periodic signals may help device performance by decreasing noise present in any individual sensor values. Because each device sensor type is different from the other types, any factors which might generate noise or degrade the performance of an individual sensor is unlikely to impact other device sensors. However, all of the device sensors may be configured to detect a single RR signal. Because of this, summing sensor data would emphasize RR while deemphasizing noise. To accomplish this, however, the time lag between the presence of the RR signal in data from different sensors must be taken into account. Air pressure will typically spike during the act of exhalation, while humidity will typically have a longer peak curve as water-saturated exhalation dissipates from the air surrounding the device. Thermopile data will typically have a delayed and still longer peak curve as the skin or other material adjacent to the exhalation path heats up during the entirety of exhalation and cools thereafter. Historical data and inherent characteristics of particular sensors can be used to design or train algorithms to better identify periodic signals, and transform different sensors' time series data so that these periods are in alignment.

Once the data has been modified, transformed and summed in a manner specific to each sensor data combination (step 425), at step 430 an autocorrelation may be calculated for each set of data (individual and combined sensor data buffers). The autocorrelation results may be analyzed for the presence and strength of a potential RR signal. For example, if a series of autocorrelation peaks exist within the frequency range of RR and above a correlation threshold representing a substantive signal, the resulting autocorrelation peak interval frequency is considered a determination of RR. In most cases, RR will be found in the calculated autocorrelation of multiple data sets (data from individual sensors or a combination of sensors).

At step 435, the sensor dataset with the most highly correlated RR signal may be considered the optimal dataset for RR determination. The sensor data set with the most highly correlated RR signal may also be considered the most valid dataset for additional respiration analysis. RRV can be calculated from the change in calculated RR over time, as well as strength of RR signal correlation within the previously calculated autocorrelation. In addition, simple peak detection can be applied to the sensor data set used to determine RR (e.g., the optimal sensor data set) and the difference in peak interval duration may supplement the calculation of RRV from the results of autocorrelation. At step 440, resulting RR and RRV determinations may be logged and/or displayed on device (10) and/or transmitted to an external device and logged or displayed on an external device.

Once RR and RRV have been determined, at step 450 processed data may be applied to models to detect respiratory events and features. The determination of sensor data significance, as well as sensor data preprocessing, are very important for respiratory event and feature models. Identification of sensor data significance can be leveraged by generating individual models specific to each possible sensor data combination or models that may be built to incorporate sensor data significance weighting.

Step 455 in FIG. 4 depicts two exemplary models. A common modeling technique for classifying high-dimensional signals in time series data is the Long Short-Term Memory (LSTM) artificial Recurrent Neural Network (RNN). LSTM may be preferred because LSTM activation functions can be more computationally efficient than other neural network models of a similar caliber, which may be important given the limited computational resources of current wearable electronic devices. The LSTM models can be trained with data that is representative of how the relevant event or feature would appear in the device's sensor data. This can be accomplished one of several ways. For example, data from the device can be collected from test subjects who exhibit respiratory symptoms while being observed, such as in a sleep laboratory. Alternatively, knowledgeable test subjects could mimic symptoms and characteristics of a particular respiratory event, such as by holding their breath to approximate sleep apnea while wearing the device.

At step 460, the resulting data can be used to train an LSTM model to distinguish between the presence or absence of, for example, sleep apnea. Instead of using training data gathered during actual device use, sensor data representing a target event could also be generated synthetically by modeling the event mathematically and transforming representative synthetically generated sensor values with this model. Such models might be trained to detect the presence of many different respiratory events and features, possibly including the diagnosis of respiratory illness or the onset of respiratory distress.

The presence of event and feature detection models may not be limited to models stored in the device when it is built and distributed. Additional models may be entered or loaded to the device's memory. Also, although LSTM models are an extremely powerful tool, there are many other modeling methods which might be used instead of or in addition to LSTM models. For example, change point detection using batch or incremental algorithms may be used. Change point detection can be further enhanced through, for example, Bayesian analysis. The methods might also be combined, as is well-established in the relevant literature.

At step 465, once an event or feature has been detected by an active model, it may be logged and/or displayed on device (10) and/or transmitted to an external device and logged or displayed on an external device. Additional information, such as the numerical output of an LSTM model and associated sensor data, may also be stored for future use.

A particular detected event, such as respiratory distress, may trigger an alarm indicating medical help is necessary. In addition, a detected event might trigger feedback to the user or another person, such as a healthcare professional. For example, a sleep apnea event might trigger a vibration motor or buzzer within device (10). Alternatively, an event may cause device (10) to transmit a signal to a nearby device or a remote device via, for example, an internet connection, which may then display or signal the event by a visual, audio, or tactile signal and/or record data from device (10). Alternatively, an event may cause a telephony device paired with device (10) to place a call or send a data message to an emergency service and/or to one or more contacts.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A system for monitoring one or more respiratory attributes of a user, comprising:
   a housing;
   an oxygen mask;
   a fastener on an outer surface of the housing, wherein the fastener is capable of attaching the housing to an outer surface of the oxygen mask when the oxygen mask is placed over the mouth of the user;
   a temperature sensor connected to the housing via an adjustable arm and capable of detecting a surface temperature of the user's skin covered by the oxygen mask when the oxygen mask is placed over the mouth of the user; and
   one or more processors located within the housing, said one or more processors configured to execute machine executable code causing the one or more processors to:
      continuously receive data output from the temperature sensor, said data indicating a surface temperature of the user's skin;
      process the data received during a first period of time to identify an initial respiration rate of the user based solely on changes in surface temperature of the user's skin during the first period of time;
      process the data received during a second period of time to identify, one or more respiratory events corresponding to one or more deviations from the initial respiration rate; and
      generate an output indicating the one or more respiratory events.

2. The system of claim 1 further comprising a digital display located within the housing, wherein the machine executable code further causes the one or more processors to display on the digital display an alert indicating the one or more respiratory events.

3. The system of claim 1, wherein the temperature sensor is a thermopile and the system is configured to locate the thermopile adjacent to a vent in the oxygen mask.

4. The system of claim 3, wherein the thermopile is situated to receive thermal radiation from the user's skin surface through the vent in the oxygen mask.

5. The system of claim 1, further comprising an air pressure sensor and the system is configured to locate the air pressure sensor adjacent to a vent in the oxygen mask.

6. The system of claim 1, wherein the one or more respiratory events are one or more respiratory disorders selected from the group consisting of Tachypnoea, Bradypnoea, Apnea, Dyspnoea, Cheyne-Stokes, Ataxic Breathing, and Hyperventilation.

7. The system of claim 1, further comprising a vibration motor, wherein the output indicating the one or more respiratory events activates the vibration motor.

8. The system of claim 1, further comprising a speaker, wherein the output indicating the one or more respiratory events causes the speaker to emit an audible sound.

9. The system of claim 1, wherein the output indicating the one or more respiratory events is transmitted to another device.

10. The system of claim 1, wherein the output indicating the one or more respiratory events causes a telephony device paired with the system to transmit a message.

11. A system for monitoring one or more respiratory attributes of a user, comprising:
    an oxygen mask having a vent;
    a temperature sensor located adjacent to the vent of the oxygen mask via an adjustable arm and capable of detecting a surface temperature of the user's skin covered by the oxygen mask when the oxygen mask is placed over the mouth of the user; and
    one or more processors located on the oxygen mask, said one or more processors configured to execute machine executable code causing the one or more processors to:
       continuously receive data output from the temperature sensor, said data indicating a surface temperature of the user's skin;
       process the data received during a first period of time to identify an initial respiration rate of the user based solely on changes in surface temperature of the user's skin during the first period of time;
       process the data received during a second period of time to identify one or more respiratory events corresponding to one or more deviations from the initial respiration rate; and generate an output indicating the one or more respiratory events.

12. The system of claim 11 further comprising a digital display located on the oxygen mask, wherein the machine executable code further causes the one or more processors to display on the digital display an alert indicating the one or more respiratory events.

13. The system of claim 11, wherein the temperature sensor is a thermopile and the thermopile is attached to the outside of the oxygen mask when the oxygen mask is placed over the mouth of the user.

14. The system of claim 13, wherein the thermopile is situated to receive thermal radiation from the user's skin surface through the vent in the oxygen mask.

15. The system of claim 11, wherein the system further comprises an air pressure sensor located adjacent to the vent in the oxygen mask.

16. The system of claim 11, wherein the one or more respiratory events are one or more respiratory disorders selected from the group consisting of Tachypnoea, Bradypnoea, Apnea, Dyspnoea, Cheyne-Stokes, Ataxic Breathing, and Hyperventilation.

17. The system of claim 11, further comprising a vibration motor, wherein the output indicating the one or more respiratory events activates the vibration motor.

18. The system of claim 11, further comprising a speaker, wherein the output indicating the one or more respiratory events causes the speaker to emit an audible sound.

19. The system of claim 11, wherein the output indicating the one or more respiratory events is transmitted to another device.

20. The system of claim 11, wherein the output indicating the one or more respiratory events causes a telephony device paired with the system to transmit a message.

* * * * *